(12) United States Patent
Robertson (10) Patent No.: US 9,974,485 B2
(45) Date of Patent: May 22, 2018

(54) METHOD AND SYSTEM FOR PROVIDING REMOTE HEALTHCARE SERVICES

(75) Inventor: James A. Robertson, The Woodlands, TX (US)

(73) Assignee: Verizon Patent and Licensing Inc., Basking Ridge, NJ (US)

(*) Notice: Subject to any disclaimer, the term of this patent is extended or adjusted under 35 U.S.C. 154(b) by 676 days.

(21) Appl. No.: 12/636,390

(22) Filed: Dec. 11, 2009

(65) Prior Publication Data

US 2011/0144451 A1  Jun. 16, 2011

(51) Int. Cl.
*G06Q 10/00* (2012.01)
*A61B 5/00* (2006.01)
*G06F 19/00* (2018.01)

(52) U.S. Cl.
CPC ............ *A61B 5/684* (2013.01); *G06F 19/321* (2013.01); *G06F 19/3418* (2013.01); *A61B 5/0022* (2013.01)

(58) Field of Classification Search
USPC .......................................... 705/2, 3; 600/300
See application file for complete search history.

(56) References Cited

U.S. PATENT DOCUMENTS

| | | | |
|---|---|---|---|
| 6,317,616 B1* | 11/2001 | Glossop | A61B 90/10 600/407 |
| 7,860,725 B2* | 12/2010 | Gopinathan et al. | 705/2 |
| 2002/0022973 A1* | 2/2002 | Sun et al. | 705/3 |
| 2002/0065461 A1* | 5/2002 | Cosman | 600/426 |
| 2006/0251408 A1* | 11/2006 | Konno et al. | 396/14 |
| 2009/0137047 A1* | 5/2009 | Regan et al. | 436/48 |

OTHER PUBLICATIONS

McClelland, J. R. (2008). Registration based respiratory motion models for use in lung radiotherapy (Order No. U591530). Available from ProQuest Dissertations & Theses Global.*

* cited by examiner

*Primary Examiner* — Lena Najarian (57) ABSTRACT

An approach is provided for healthcare information management and providing remote healthcare examination. A platform receives position data corresponding to a mark to be projected onto a human subject by a user equipment. The mark specifies placement of a medical sensor onto the subject. The platform collects measurement data from the medical sensor coupled to the subject at the mark.

22 Claims, 8 Drawing Sheets

METHOD AND SYSTEM FOR PROVIDING REMOTE HEALTHCARE SERVICES

BACKGROUND INFORMATION

Improvements in communication networks and consumer adoption of telecommunication devices have fueled the growth of delivery of health-related services and information via communication technologies. Remote examination services or tele-visits can supplement in-person visits to medical professionals offices such that patients and medical professionals are at remote locations during an examination, for example. However, the development of health-related services, such as remote examination, have lacked the needed precision, in large part, because the interaction between patients and medical professionals have been limited by traditional telemedicine techniques.

Therefore, there is a need for an approach for improved interactivity and accuracy in telemedicine services.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF THE PREFERRED EMBODIMENT

A preferred apparatus, method, and system for providing remote healthcare services are described. In the following description, for the purposes of explanation, numerous specific details are set forth in order to provide a thorough understanding of the preferred embodiments of the invention. It is apparent, however, that the preferred embodiments may be practiced without these specific details or with an equivalent arrangement. In other instances, well-known structures and devices are shown in block diagram form in order to avoid unnecessarily obscuring the preferred embodiments of the invention.

Figure 1:
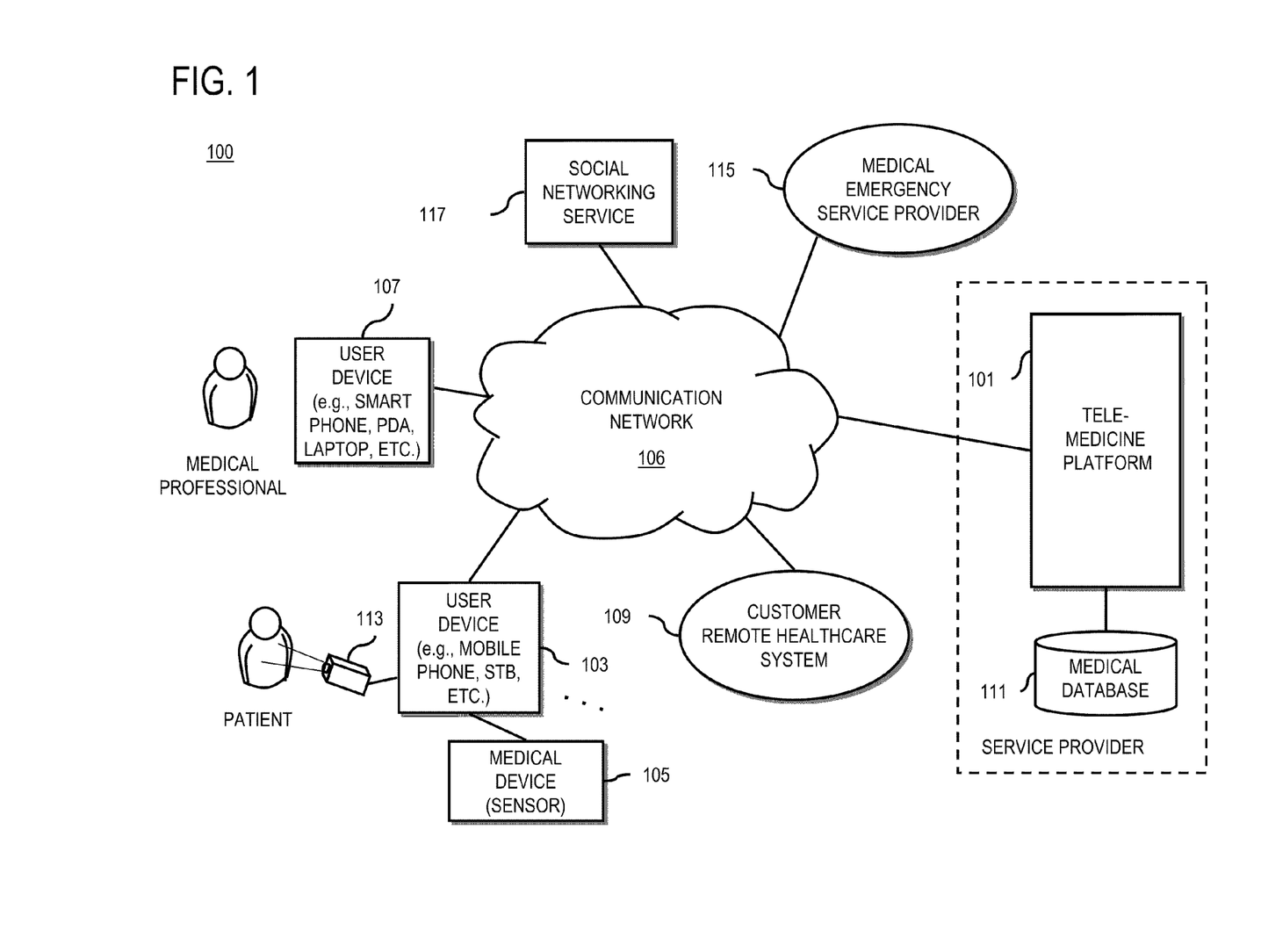
FIG. 1 is a diagram of a system capable of providing healthcare management and remote healthcare examination services, according to an exemplary embodiment.

FIG. 1 is a diagram of a system capable of providing healthcare management and remote healthcare examination services, according to an exemplary embodiment. As shown, system 100 includes a telemedicine platform 101 that can support a variety of telemedicine services, such as, home monitoring, remote visits, remote examination, managing medical emergency services, etc. To access such services, a user may employ a user device 103 in conjunction with a medical device or sensor 105 to collect data for submission to the telemedicine platform 101 over a communication network 106. As an example, for remote healthcare examination, a host of equipment, such as television displays, personal computers, and mobile devices, can support user interfaces for remote visits. In this context, according to certain embodiments, the telemedicine platform 101 provides the capability to present user interfaces over user device 103 to a user (e.g., a subscriber, a patient, etc.) as well as a medical professional via user device 107 (e.g., a tablet PC, Personal Digital Assistant (PDA), a mobile phone, smart phone, laptop, web appliance, etc.) in support of a communication session for remote healthcare examination. The medical professional, for example, can be a doctor, a nurse, a technician, a paramedic, or any person that can properly instruct the user on how to utilize medical equipment, device, or sensor.

As mentioned, conventional systems have been constrained by the types of medical data that can be sensed and collected. Also, accuracy of the data is compromised if the sensing equipment is not properly installed and applied. To improve accuracy, conventionally, it may require dispatching a medical professional to set-up the medical devices and train the users; however, this entails additional costs and reduces the convenience associated with telemedicine in the first place. Therefore, the approach of system 100, according to certain exemplary embodiments, stems from the recognition that a more interactive and intuitive interface is needed to improve the gathering of accurate data about the person being monitored (i.e., patient).

In one embodiment, the telemedicine platform 101 can be managed and operated by a single service provider to offer the remote healthcare examination as a managed service. Alternatively, it is contemplated that the telemedicine platform 101 can be operated as a distributed platform, involving different entities. Further, the platform 101 can be deployed at a user (or customer) premise, such that the platform 101 is managed by the customer. In this customer implemented system, the medical professional is remotely located, but the patients can be housed in a facility of the customer.

For the purpose of illustration, the telemedicine platform 101 provides a home monitoring capability that medical measurements and diagnostic results associated with a user (such as a patient) are stored and managed in a centralized repository 111. In this example, the telemedicine platform 101 provides a virtual session for remote examination between a user (e.g., patient) and a medical professional. The session is deemed to be "virtual" in the sense that the medical professional is not physically present with the patient. Remote examination virtual session can be in addition to and/or instead of in-person visits to medical professionals. During the virtual session, the telemedicine platform 109 can receive requests from the medical professional for medical measurements associated with the user. Measurement data can be obtained from various medical sensors and/or medical devices, such as medical thermometer, blood sugar meter, blood pressure meter, external pacemaker, ultrasound sensors, stethoscope, etc. The telemedicine platform 109 can capture or receive captured image of a user and store and/or transmit the image to the device 107 of the medical professional. As discussed, sensor data or information can be inaccurate if the medical sensor is not implemented properly. That is, inaccurate or incomplete sensor information can stem from incorrect placement of the sensor itself. For instance, in the case of a stethoscope, many users may not know precisely where to place the instrument on the body to optimize measurement of the heart beats, or to diagnose the condition of the lungs.

In recognition of this drawback, the tele-medicine platform 101 is configured to enable the medical professional to precisely indicate to the patient where the sensor 105 should be situated on the patient. According to certain embodiments, a projection device 113, under the control of the user device 107 of the medical professional can specify a mark (or other indicia) as an image that is projected onto the user to indicate the position where the medical device or sensor 105 is to be positioned. The telemedicine platform 101 can receive position data via the user device 107 that corresponds to the mark, which is specified by the medical professional. The telemedicine platform 109 can capture measurement data from the medical device 105, which is coupled to the user at the projected mark. Once situated, the sensor or measurement data is collected by the user device 103 and transmitted to the platform 101 and then relayed to the device 107 of the medical professional for diagnosis or examination. The medical measurement data can be stored in the medical database 111. In one exemplary embodiment of the telemedicine platform 101, the medical professional (e.g., doctor) would be able to view, on their computer display, the image of the patient as captured by a video camera at the patient site. The medical professional can "draw" a mark (such as an "X") on the patient's image using a standard computer input device (such as mouse, or electronic tablet stylus); and this mark would be projected upon the patient's person via projector device, being visible to both the doctor and persons at the patient site. Such mark serves as an indicator of where the patient or assisting party should position the medical diagnostic device (for example, an electronic stethoscope). Under this arrangement, the doctor can effectively remotely draw a figure on the patient's person to guide the positioning of the diagnostic device, and they can erase such figure and draw another at a new position, as they instruct the patient (or assisting party) to move the sensor to different locations. In one exemplary embodiment, the sensor could be an electronic stethoscope, and the medical professional would be able to listen to the captured sounds from the sensor via audio headphones of loudspeaker.

In some embodiments, the platform 101 can make necessary adjustments of the position and scaling of the mark to compensate for the patient's movements. Under such a scenario, the user device 103 can be equipped with a video camera (e.g., web cam) to capture small movements of the user. The movements are detected and modification to the position of the mark is made, and projected onto the user. This capability is particularly useful when the user is an adolescent, who is prone to fidget during medical procedures.

Additionally or alternatively, the platform 101 can instruct the user device 107 of the medical professional to directly receive the measurement data. According to one embodiment, the telemedicine platform 109 can identify, in the case of multiple users, which user is utilizing the medical device 105, whereby the received diagnostic results are properly associated with the correct user. Further, the collected data can be readily distributed to or accessed by other medical professionals It is contemplated that the user devices 103 and 107 can communicate wirelessly or over a wired connection using communication 107.

By way of example, communication network 106 may include one or more networks such as a data network and/or a telephony network. It is contemplated that the data network may be any local area network (LAN), metropolitan area network (MAN), wide area network (WAN), a public data network (e.g., the Internet), or any other suitable packet-switched network, such as a commercially owned, proprietary packet-switched network, e.g., a proprietary cable or fiber-optic network. Moreover, the telephony network can be provided via a combination of circuit-switched technologies or a packetized voice infrastructure.

By way of example, communication network 106 can include a radio network that supports a number of wireless terminals, which may be fixed or mobile, using various radio access technologies. According to one exemplary embodiment, radio technologies that can be contemplated include: first generation (1G) technologies (e.g., advanced mobile phone system (AMPS), cellular digital packet data (CDPD), etc.), second generation (2G) technologies (e.g., global system for mobile communications (GSM), interim standard 95 (IS-95), etc.), third generation (3G) technologies (e.g., code division multiple access 2000 (CDMA2000), general packet radio service (GPRS), universal mobile telecommunications system (UMTS), etc.), 4G, etc. For instance, various mobile communication standards have been introduced, such as first generation (1G) technologies (e.g., advanced mobile phone system (AMPS), cellular digital packet data (CDPD), etc.), second generation (2G) technologies (e.g., global system for mobile communications (GSM), interim standard 95 (IS-95), etc.), third generation (3G) technologies (e.g., code division multiple access 2000 (CDMA2000), general packet radio service (GPRS), universal mobile telecommunications system (UMTS), etc.), and beyond 3G technologies (e.g., third generation partnership project (3GPP) long term evolution (3GPP LTE), 3GPP2 universal mobile broadband (3GPP2 UMB), etc.).

Complementing the evolution in mobile communication standards adoption, other radio access technologies have also been developed by various professional bodies, such as the Institute of Electrical and Electronic Engineers (IEEE), for the support of various applications, services, and deployment scenarios. For example, the IEEE 802.11 standard, also known as wireless fidelity (WiFi), has been introduced for wireless local area networking, while the IEEE 802.16 standard, also known as worldwide interoperability for microwave access (WiMAX), has been introduced for the provision of wireless communications on point-to-point links, as well as for full mobile access over longer distances. Other examples include Bluetooth, ultra-wideband (UWB), the IEEE 802.22 standard, etc.

As part of the healthcare management and remote examination service, the user medical device 105 can, directly or indirectly (e.g., through user device 103), be in communication with communication network 106. Therefore, medical measurements and diagnostic results, measured by user medical device 105, can be sent to the telemedicine platform 109 through communication network 106. The diagnostic results can be processed in the telemedicine platform 109 and/or be stored in the medical database 111. Therefore, medical professionals can view and follow user diagnosis data, spanning large time intervals instead of a snap-shot of user during a single office visit, for instance.

Moreover, the telemedicine platform 109 can maintain one or more portals (which may be web-based) for patients and medical professionals to permit access to the patients' information. The user portal provides users, e.g., patients, with the capability to conveniently access and manage their respective profiles including medical records and diagnostic data derived from the sensors. The medical professional portal permits medical professionals to conveniently access the patients' information.

As mentioned, telemedicine platform 109 can provide remote visits to supplement in-person visits to medical professional's office. Under this scenario, the telemedicine platform 101 can configure the user portal and the medical professional portal to provide services such as pre-screening, obtaining patient information (e.g., on-line forms), etc. in advance of an in-person appointment.

Alternatively, the virtual sessions, or tele-visits, can replace a visit to the doctor's or hospital altogether. At times, particularly when the condition of the user/patient does not warrant being exposed to more seriously ill patients at the hospital (e.g., such patients may be contagious), a pure tele-visit would pose less of a health threat, and provide greater convenience to the user. Furthermore, in regions of the world that are underserved by medical professionals, the remote medical diagnostics platform can help augment the reach of medical workers to greater numbers of patients.

Moreover, in support of these remote visit services, the platform 101 can present a graphical user interface (GUI) with interactive graphics, e.g., via the portals, to perform pre-screening tasks. The user (or patient) portal can provide an interactive anatomical drawing for the user to indicate an area that is experiencing pain, for instance, or is potentially injured. Also, the platform 101 can provide multimedia interaction (synchronous or asynchronous) (such as voice, video, chat, etc.) to facilitate communication between the user and the medical professional. Additionally, the portals can support on-line fillable forms (in which certain data can be pre-filled automatically by the platform 101). The user 103 can thus fill out the necessary forms in advance of the appointment, thereby minimizing the time at the doctor's office as well as eliminate the inconvenience filling out a paper form. Also, the pre-filled form capability ensures greater accuracy of the information.

To expedite the doctor visit, the telemedicine platform 109 can also offer a virtual session capability as part of remote visit services. The medical professional, using the device 107, can communicate with the user concerning the manner in which the medical device 105 can be applied to obtain accurate and complete medical measurements. In one example, the user via user device 103 and the medical professional via device 107 can communicate using a video communication session established over the network 106.

In certain embodiments, telemedicine platform 101 can support a medical emergency service provider 115. In this manner, a device (not shown), which can integrate the capabilities of projector 113 (which may be a pico-projector) and user device 103, can be deployed out in the field by medical professional, e.g., paramedics; such device can also be configured to communicate wirelessly with the telemedicine platform 109 through the communication network 106. For instance, the projector 113 can be fitted into the user device 103, which may a mobile phone (e.g., mobile phone of FIG. 7). Alternatively, this emergency medical device (such as a defibrillator) can be located in a public place for access by the person requiring emergency care or another user who may assist the person in need of care. In case that this public medical device is used, the telemedicine platform 101 can detect such usage and notify the medical emergency service provider 115 so that emergency services can be dispatched to the location of the public medical device.

Furthermore, the telemedicine platform 101 can interact with a social networking service 117, which can be implemented as a website. In this manner, the service 117 can provide a medium for users and medical professional to access, maintain, and view user records (e.g., medical and diagnostic records), share information, access articles related to health and lifestyle, etc. In the alternative, the platform 101 can itself supply the social networking service or be integrated with one that is maintained by the service provider.

Although the example of FIG. 1 describes the telemedicine platform 101 as a separate entity from the user devices 103 and 107, it is contemplated that some or all of the functions of the platform 101 may be employed within these devices 103 and 107 depending on the particular implementation.

Exemplary components of the telemedicine platform 101 are more fully described below.

Figure 2:
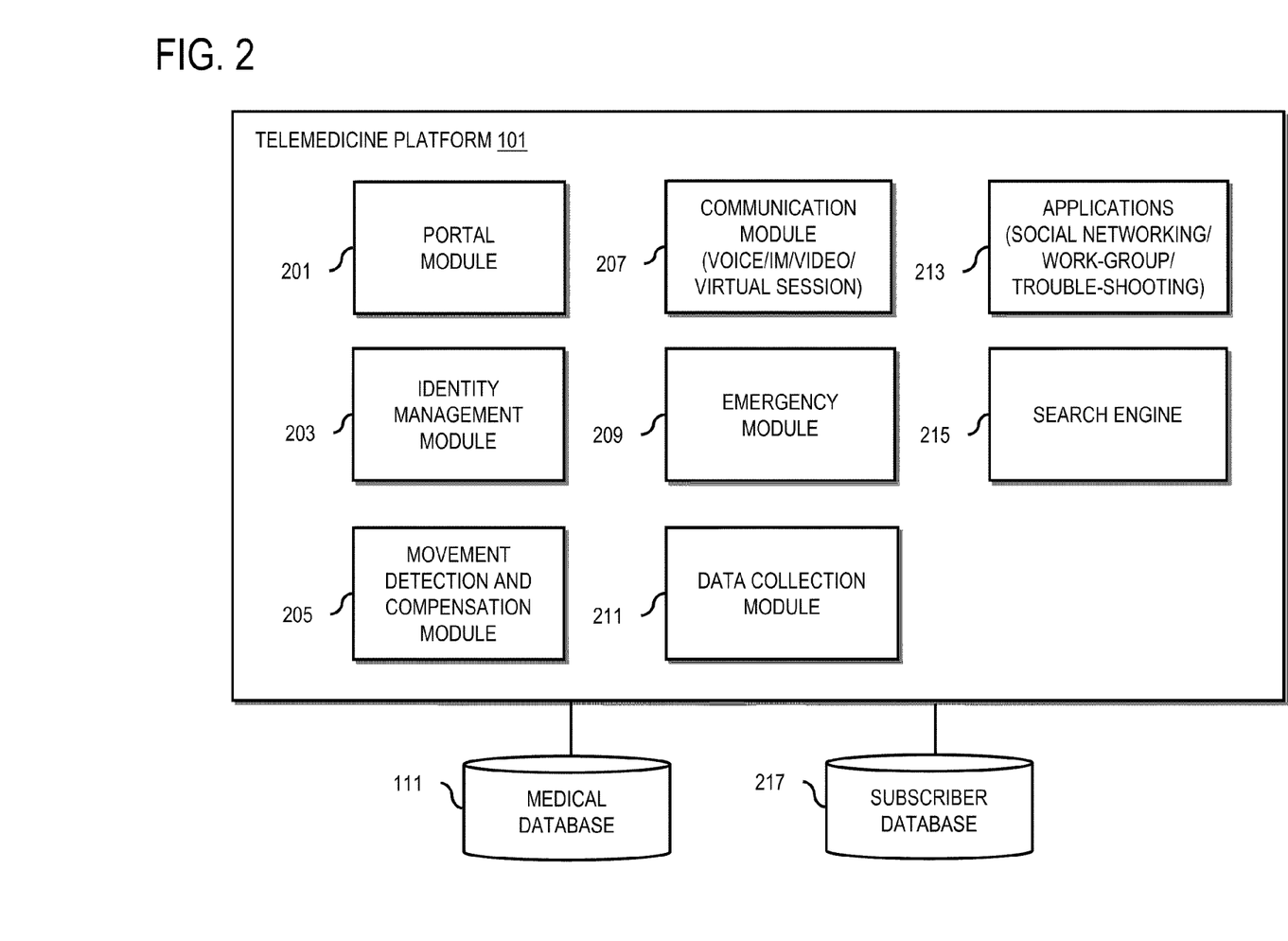
FIG. 2 is a diagram of components of telemedicine platform in the system of FIG. 1, according to an exemplary embodiment.

FIG. 2 is a diagram of components of telemedicine platform 109 in the system of FIG. 1, according to an exemplary embodiment. For the purpose of illustration, the telemedicine platform 109 can include various components: a portal module 201, an identity management module 203, a movement detection and compensation module 205, a communication module 207, an emergency module 209, a data collection module 211, one or more applications 213, and a search engine 215. Effectively, these components support several telemedicine related services provided by the telemedicine platform 109 including home monitoring, remote visits, and managing medical emergency services. Under a managed services configuration, the platform 101 includes a subscriber database 217 to store user profiles and associated account information.

The portal module 201 can be configured to manage and operate the user and medical professional portals as described above. These portals, which may be implemented as a single or multiple websites, can include graphical user interfaces for the user (e.g., patient) and the medical professional to upload, view, and access different medical information, provide pre-screening options, offer forms, support home monitoring, initiate communication between user and medical professional, initiate and manage virtual session for remote examination, etc. The portal module 201 can be operatively connected to the medical database 111 to store and access user medical information. Additionally, the portals can present interactive graphics such that users and/or medical professional can use anatomical drawings to explain medical issues and/or specify locations that medical sensors need to be placed (in conjunction with the more precise indication by the projection of the mark).

The virtual sessions (or meetings) between the medical professional and the patient can be conducted through the portal module 201. In the case of a remote examination virtual session, the medical professional can access, using device 107, the medical professional portal, which can launch a communication session with the user via user device 103. This portal can then control the user device 103 and associated projector 113 to guide the user in applying the medical device 105. Once deployed properly, the medical device 105 can output medical information or data.

Alternatively, the user devices 103 and 107 can independently establish communication between the medical professional and the patient without the assistance of the communication module 207. For instance, the medical professional and the user can engage in a video conferencing session through a separate video conferencing system provided by the user devices 103 and 107. Under this scenario, the telemedicine platform 101 can simply facilitate the processes of marking the patient and data collection.

In one embodiment, this medical information includes sensor data from medical device 105.

The collection of this information is the responsibility of the data collection module 211. In one example, the data collection module 211 can further process the collected data; for example, statistical analysis of the measurement data can be performed to determine trends for medical professionals to aid with diagnosis.

In this example, data collection module 211 can receive image data corresponding to the user. The image data can be stored and sent to the medical professional's device 107 and be presented to the medical professional via a graphical user interface. The medical professional uses the graphical user interface to specify a mark on the image of the user corresponding to a location where the medical sensor is to be placed. The device 107 of the medical professional generate position data associated with the mark specified by the medical professional, and generate a request for medical measurement data (such request can include the position data).

As noted, the set-up of the user device 103, the medical device 105 and projector 113 can be utilized by multiple users, e.g., different family members within a single home. Accordingly, the platform 101 uses the identity management module 203 to ensure that the collected medical data received from the user medical devices (such as the user medical device 105 of system 100) is associated with the correct user. In one embodiment, the identity management module 203 instructs the user device 103 to perform an authentication procedure, such as a user identification (ID) and password prompt to the user. Alternatively, more sophisticated methods can be employed, such as biometric identification, etc.

In one embodiment, the telemedicine platform 109 includes a movement detection and compensation module 205 to track small movements of the user 103 and reposition the mark that is projected onto the user. In one embodiment, the data collection module 211 can capture and/or receive captured images of the user. The collected images are compared to the stored image of the user. The movement detection and compensation module 205 can determine movement of the user based on the comparison and therefore, can dynamically (e.g., in near real-time or real-time) reposition the mark that is projected on the user based on the determined movement. In one exemplary embodiment of the movement detection and compensation mechanism, a two-dimensional cross-correlation between the image stored when the mark is drawn and the subsequent collected images would serve to detect and quantify patient lateral movements, and allow the mark to be dynamically re-positioned so as to keep it at a relatively fixed position on the patient's person.

Further, the telemedicine platform 101 includes the communication module 207, which can support one or more of various communication sessions. According to one exemplary embodiment, the communication module 207 can set up and manage voice, video, and/or chat communication between the user and the medical professional, or with either party separately.

As explained, the telemedicine platform 101 can support emergency medical services using the emergency module 209. Namely, the emergency module 209 can receive a signal corresponding to a public medical device (not shown), which is connected to the communication network 106, when the public medical device is used. In one example, the emergency module 209 can inform the medical emergency service providers (such as medical emergency provider 119 of system 100) when it receives the signal. Additionally, the emergency module 209 can detect the location of the public medical device based on the received signal.

Further, the telemedicine platform 109 can utilize various applications 213 that can complement the telemedicine services. For example, the applications 213 can include a social networking application to offer a medium for users and medical professionals to access, maintain, and view user records (e.g., medical and diagnostic records), share information, access articles related to health and lifestyle, etc. In effect, the platform 101 runs a social networking service; alternatively, the social networking application can interface the social network service 117, which is operated and maintain by a third party. Also, the applications 213 can include work-group collaboration application and/or trouble-shooting application to provide a work-group collaboration space for solving the users' medical and/or administrative issues. As such, a user can report a medical issue, whereby a collaboration space is created (with initially just the user and a first point of contact). As the medical issue is being resolved, additional medical professionals and subject matter experts can be added to the space. The collaboration space can be active until user's issue is addressed to the user's satisfaction.

The telemedicine platform 109 includes a search engine 215 to perform searches on the medical database 111 for resources, providers, access to user medical record, etc. telemedicine platform 109 can also be used to perform searches regarding user information and/or medical record, resources, and/or providers. The search engine 215, which can operatively be connected to the databases 111 and 219, is used to initiate searches.

Different components of the telemedicine platform 109, as a distributed platform, can be allocated in different devices of the system 100. In one exemplary embodiment, the communication module 207, the data capture module 211, and/or the movement detection and compensation module 205 can operate in a user device (such as user device 103), a set-top box (not shown), and/or a combination thereof.

Figure 3:
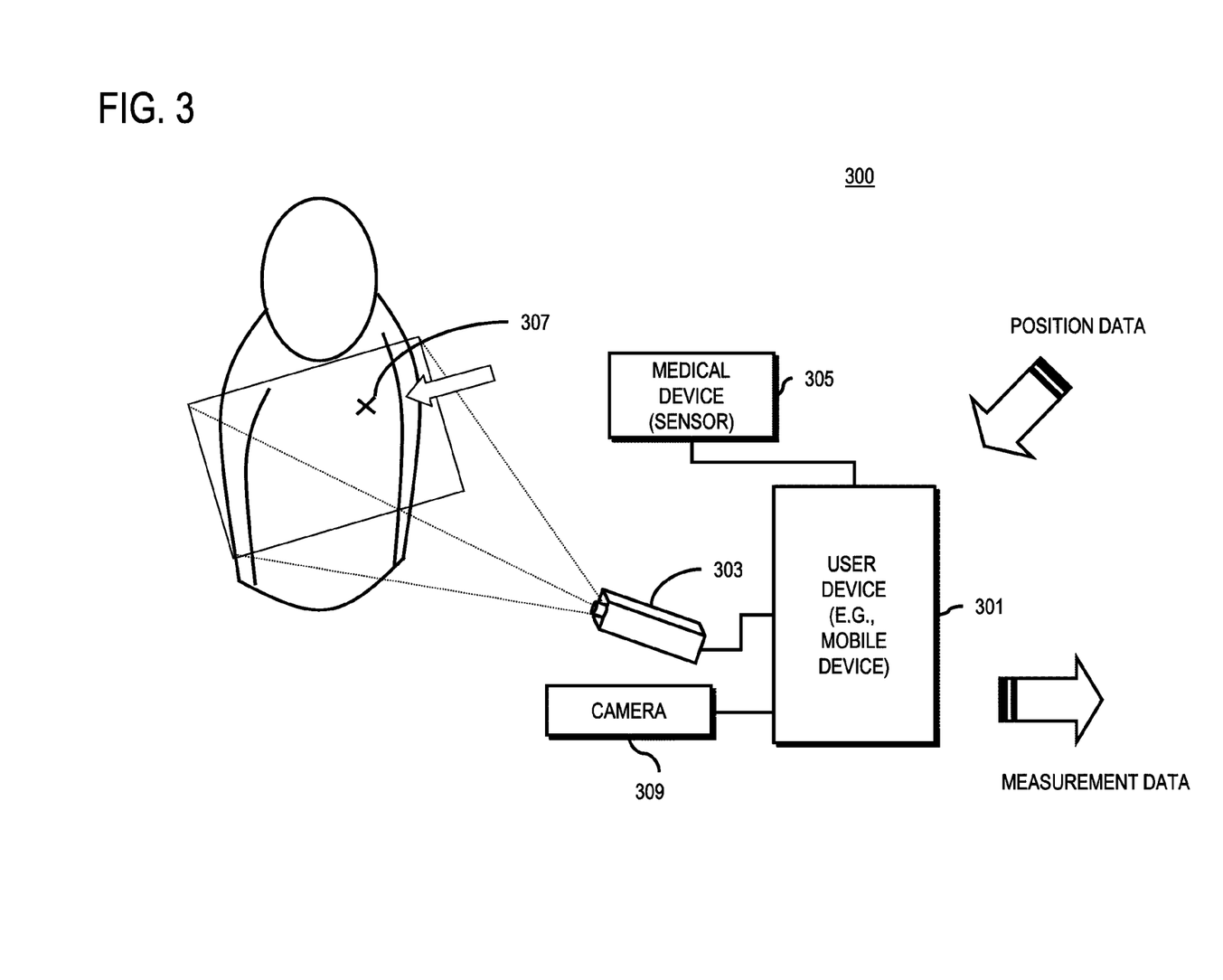
FIG. 3 is a diagram of a system capable of projecting a mark for obtaining measurement data, according to an exemplary embodiment.

FIG. 3 is a diagram of a system capable of projecting a mark corresponding to position data, according to an exemplary embodiment. For the purposes of explanation, this system 300 includes a user device 301 coupled to or integrated with a projector 303. A medical device (or sensor) 305 interfaces, using wired or wireless technology, with the user device 301 to gather measurement (or sensor) data output from the medical device 305. The user device 301 controls the projector 303 in response to one or more commands provided remotely from a medical professional. In particular, the commands include position data of where to project an image 307 of a mark onto the user for placement of the medical sensor 305. Effectively, the medical professional can precisely direct the user on positioning of the medical sensor 305.

To permit accurate placement of the sensor, a camera 309 is utilized for real-time capturing images of the user, wherein these images are presented to the medical professional for designation of the mark 307. The camera 309 can be configured to directly communicate with the platform 101 over the communication network 106 of system 100 or be operatively connected to the user device 301. According to certain embodiments, the camera 309 can be part of a mobile device that is separate from the user device 301. In the alternative, the user device 301 is the mobile device, which houses both the camera 309 and the projector. However, as shown, the camera 309 and the projector 303 can be housed in separate devices.

Sensor measurement data output by the sensor are collected and transmitted to the telemedicine platform 101. The telemedicine platform 101, in turn, transmits this measurement data to the user device of the medical professional for examination and analysis.

Figure 4:
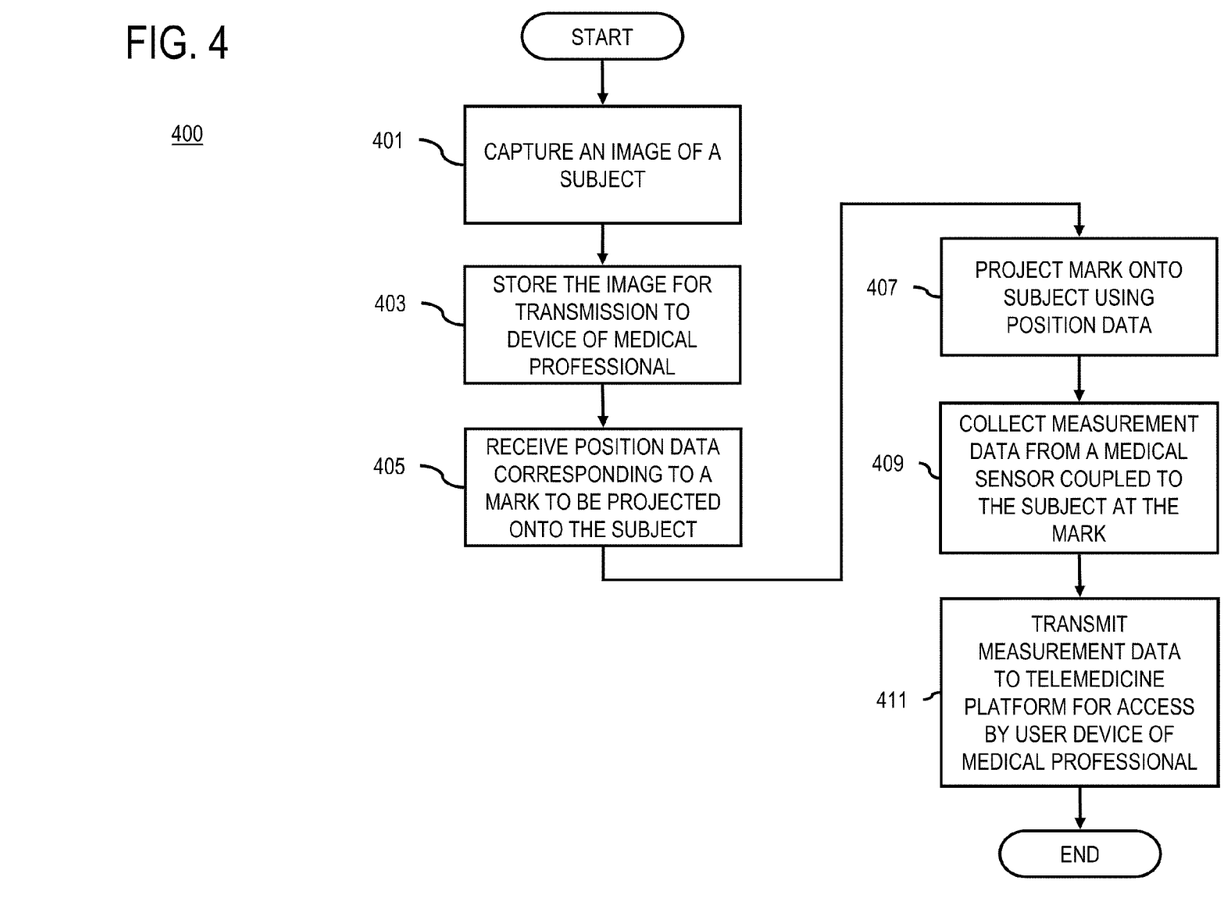
FIG. 4 is a flowchart of a process for remote examination, according to an exemplary embodiment.

FIG. 4 is a flowchart of a process for remote examination, according to an exemplary embodiment. By way of example, process 400 is performed at the telemedicine platform 101 (of FIG. 1) in communication with user devices 103 and 107. At step 401, an image of the subject is captured by the user device 103 using a camera (e.g., camera 309 of FIG. 3); this image is stored, per step 403, for transmission to user device 107. In one embodiment, the user device 103 is a set-top box, which is configured to perform all or part of the functions/tasks associated with the virtual session for the remote examination. Next, the device 107 presents a GUI to the medical professional for specifying where a mark should be projected onto the subject. The device 107 thus receives the image of the user; and the graphical user interface presents the received image to the medical professional. The medical professional subsequently indicates a mark, using GUI, on the image of the user. The mark corresponds to a location where the medical device or sensor 105 will be placed. That is, the medical professional designates where the medical device 105 is to be situated on the user by selecting an area within the image. Position data associated with the selected area is generated, and transmitted from the user device 107 to user device 103 either directly or via the telemedicine platform 101. For example, the medical professional can "draw" or otherwise designate marks (such as an "X" or "O") on the received image of the user. This mark, or "digital ink," can appear on the skin of the user, as projected by the projector 113.

Position data can be generated from the mark specified by the medical professional. The position data corresponds to the location of the mark on the body of the user and is used in the user side to project a mark on user body. In one exemplary embodiment, the position data can include coordinates (or pixel locations) associated with the mark in an image plane corresponding to the received image according to a coordinate system. However, it is contemplated that any process to generate the position data based on the mark specified by the medical professional can be used.

Thus, the user 103 can locate the medical sensor 105 on the user's body according to the projected mark (associated with the position data). Medical measurements output by the sensor 105 can be captured by the telemedicine platform 101 for processing, storage, and/or transmission to the medical professional device 107. This process can be repeated until the medical professional has gathered the necessary information for the remote examination.

For example, the medical professional (e.g., doctor) can remotely specify a marking, image, or picture on the patient's skin (and erase them with a click of a mouse, for example). The doctor can indicate to the patient the position for placement of the stethoscope at the "X" and also tell the patient to breathe deeply. Subsequently, the doctor can erase the mark and draw another mark at a new location for repositioning the stethoscope. In effect, the interactivity mimics that of a real, physical doctor's visit, where diagnosis would be based on accurate sensor data.

In one embodiment, the GUI can be presented as part of the portal provided by the platform 101, as discussed above. It is noted that the telemedicine platform 101 can initiate download of any necessary application (e.g., client software) to be executed by the device 107 of the medical professional for assisting with the virtual session with the subject. Consequently, the telemedicine platform 101 can behave as a server process to lead the user and the medical professional through the data collection.

At step 405, position data that corresponds to the mark specified by the medical professional is received by the user device 103. The mark is projected, as in step 407, by the projector 113 onto the subject using the position data. In one embodiment, the telemedicine platform 109 can transmit the received position data, through the communication network 106, to the user device 103. Alternatively or additionally, the telemedicine platform 109 can operate as a distributed platform, and therefore, logic operating at the user device 103 can receive the position data from the medical professional's device 107 directly through the communication network 106.

At step 409, the medical measurement data is collected from the medical sensor 105 that is coupled to the subject at the projected mark. The data is uploaded to the telemedicine platform 101 for access by user device 107 of the medical professional, per step 411. The collected measurement data can then be analyzed by the medical professional.

The platform 101 can also account for movements of the user to ensure accurate alignment of the mark, as next detailed.

Figure 5A:
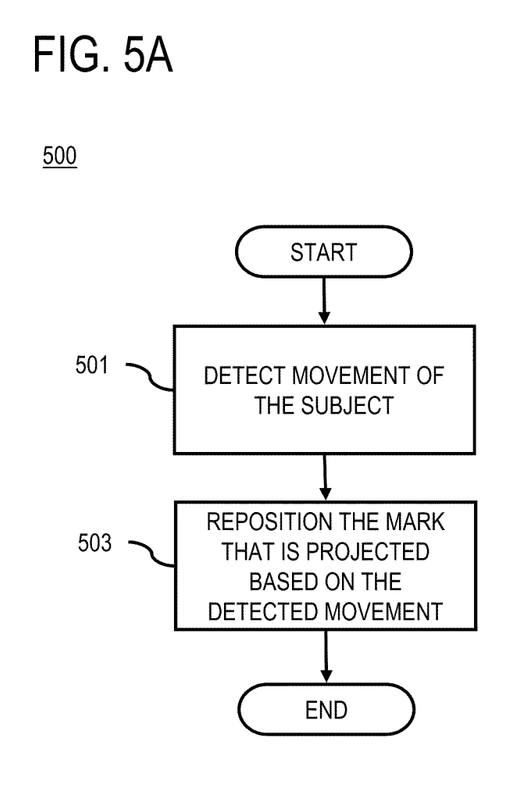
FIGS. 5A and 5B are flowcharts of a process for movement detection and compensation to provide remote examination, according to various exemplary embodiments.
Figure 5B:
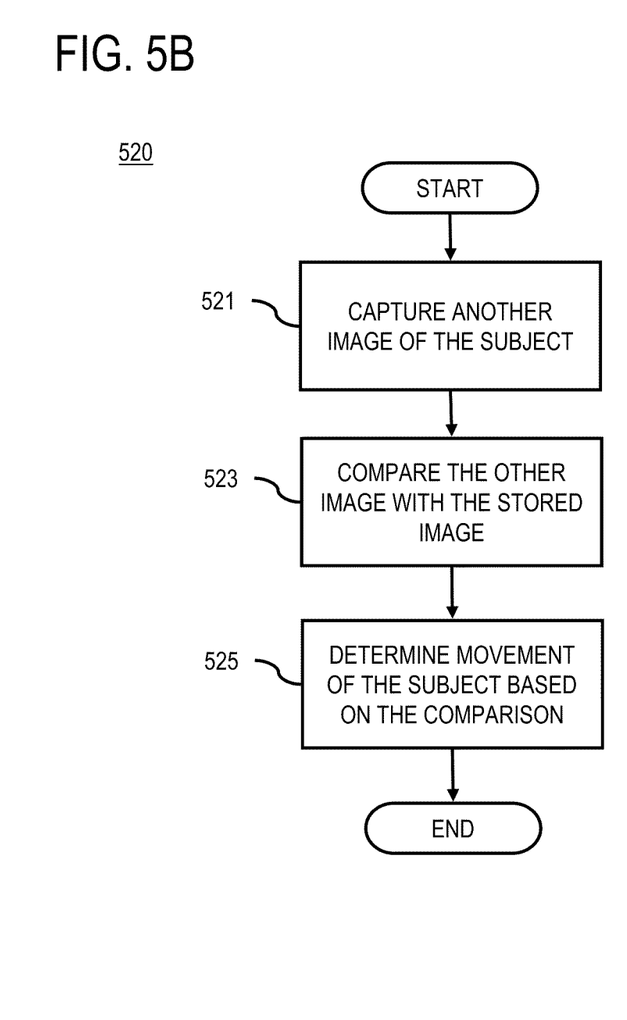

FIGS. 5A and 5B are flowcharts of a process for movement detection and compensation to provide remote examination, according to various exemplary embodiments. In one embodiment, the processes 500 and 520 are performed at the telemedicine platform 101 of system 100 and more specifically by the movement detection and compensation module 205 (shown in FIG. 2). The process 500 is performed to track movements (e.g., within the field of view of the camera) of the subject and compensate the position data based on the detected movement in order to reposition the mark that is projected on the user. At step 501, the process 501 can detect movement of the subject, such as the user 103. The mark is projected on the subject at a new location based on the detected movement, per step 503.

It is contemplated that various techniques for determining movement can be utilized. As seen in FIG. 5B, the process 520, at step 521, captures another image of the user (and/or receives another captured image of the user). At step 523, the captured image is compared to the stored image. Based on the comparison, at step 525, the process 520 can determine the movement of the subject.

Alternatively, one or more reference marks can be provided on the subject (e.g., the user 103). The movement detection and compensation module 205 can then track position of the one or more reference marks and determine the positional adjustment to the position data corresponding to the mark. In another example, one or more objects surrounding the subject that are fixed with respect to the subject can be determined; and the movement of the subject can be determined by the positional difference of the subject with respect to the one or more fixed objects in different images. Additionally or alternatively, the data collection module 211 can capture and store an image of the subject with the mark when the medical professional specifies the mark. Further, the data collection module 211 can capture current image of the subject and perform a cross-correlation between the current image and the stored image with the mark to determine the positional movement of the subject.

The process 520, in one embodiment, can detect when the medical sensor is applied, which is a condition for terminating the process 520. That is, once the sensor is correctly positioned onto the subject, the platform 101 need not attempt to compensate for any further movement.

Figure 6:
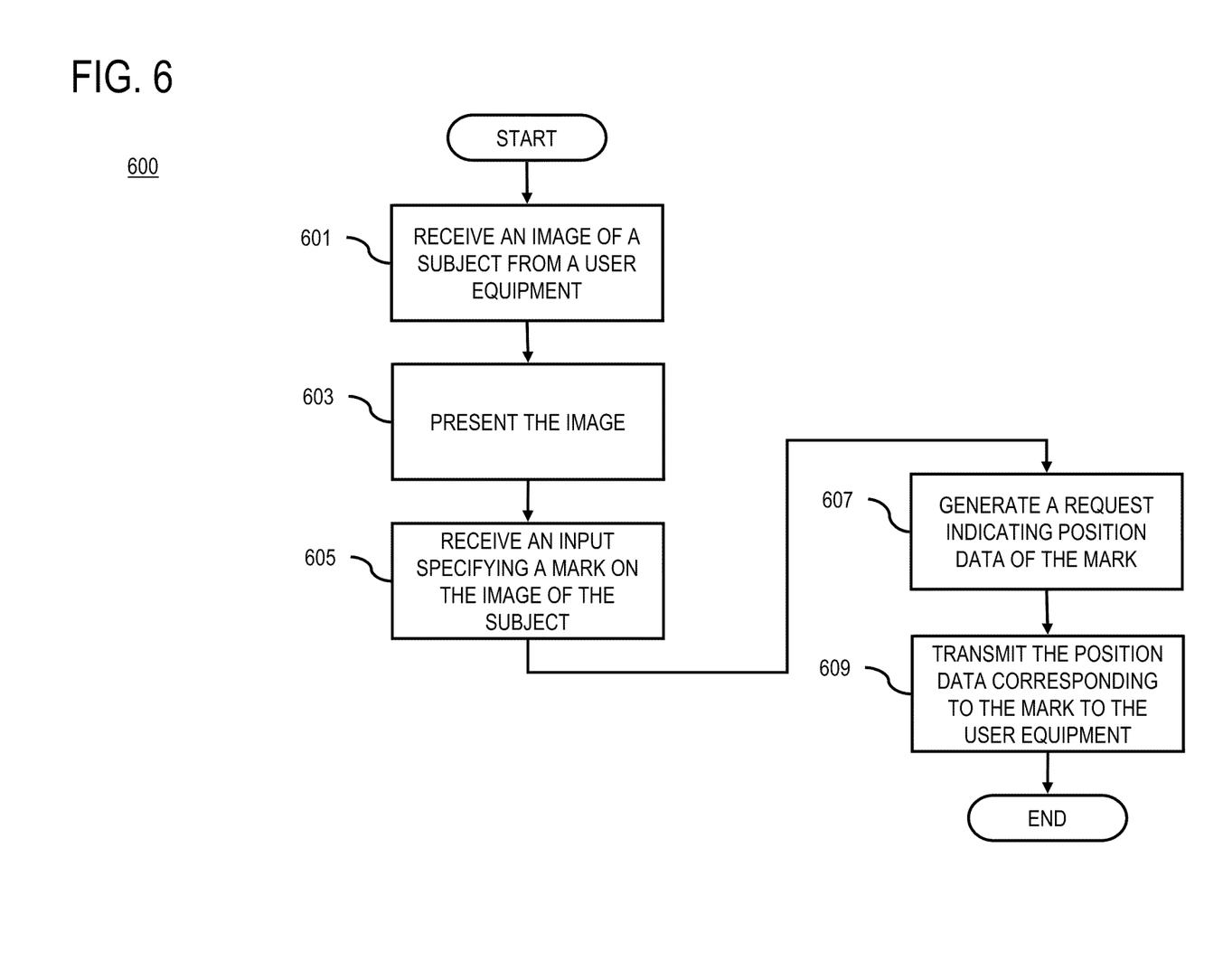
FIG. 6 is a flowchart of a process for generating and transmitting position data for projecting a mark, according to an exemplary embodiment.

FIG. 6 is a flowchart of a process for generating and transmitting position data for projecting a mark, according to an exemplary embodiment. In one embodiment, the process 600 is performed at the device 107 of the medical professional with system 100. At step 601, the process 600 receives an image of a subject from user equipment. For example, the image of the user captured by a user device (such as user device 103) is received at the device 107. At step 603, the received image of the subject is presented via the user device 107 using a graphical user interface.

At step 605, the process 600 receives, from the medical professional, an input, that specifies a mark on the received image of the subject. In one example, the medical professional can use the device 107 to indicate a point on the image of the user where the mark is to be projected. At step 607, the process 600 generates a request that indicates the position data of the mark as specified by the medical professional. Next, the request (including the position data) is transmitted, as in step 609, to the user device 103 for projecting the mark onto the patient using the projector 113. At this point, the user may position the medical sensor 105 to capture measurement data.

It is contemplated that multiple medical sensors can be utilized, whereby multiple marks can be projected onto the user for collecting sensor data concurrently from these sensors.

The described processes and arrangement, according to certain embodiments, can accurately provide collection of medical sensor information, thereby enabling greater deployment of telemedicine services. Also, telemedicine platform 101 can reduce actual time for in-person visits by providing pre-screening services, such as automated on-line forms. Further, the platform 101 permits long-term storage of readily accessible medical data; as such, diagnosis of the patient's condition is enhanced.

Figure 7:
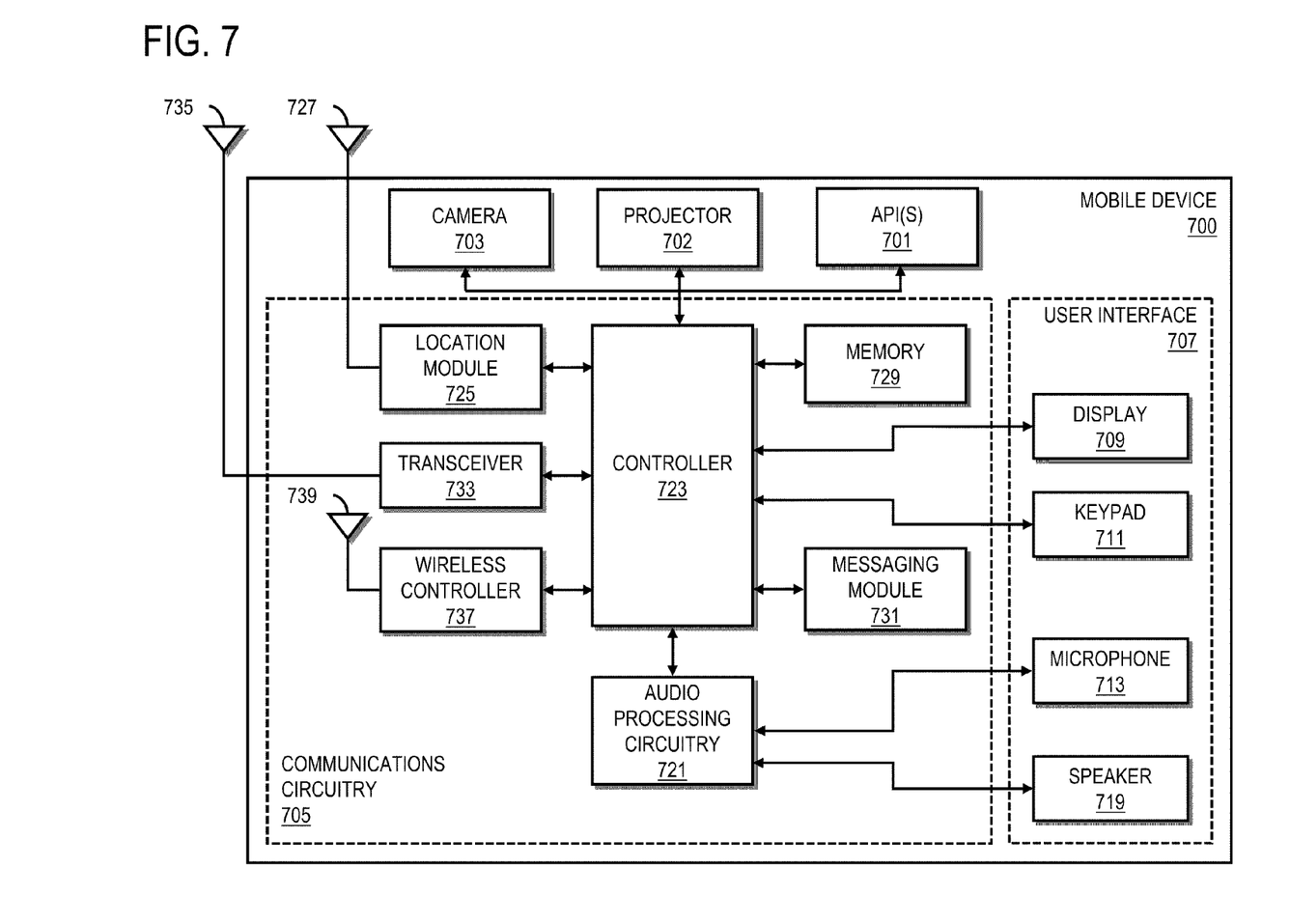
FIG. 7 is a diagram of a mobile device configured to project a mark for collecting sensor data, according to an exemplary embodiment.

FIG. 7 is a diagram of a mobile device configured to project a mark for collecting sensor data, according to an exemplary embodiment. Mobile device 700 may comprise computing hardware (such as described with respect to FIG. 8), as well as include one or more components configured to execute the processes described herein for facilitating the telemedicine services of system 100. In this example, mobile device 700 includes application programming interface(s) 701, a projector 702, camera 703, communications circuitry 705, and user interface 707. While specific reference will be made hereto, it is contemplated that mobile device 700 may embody many forms and include multiple and/or alternative components.

According to exemplary embodiments, user interface 705 may include one or more displays 709, keypads 711, microphones 713, and/or speakers 715. Display 709 provides a graphical user interface (GUI) that permits a user of mobile device 700 to view dialed digits, call status, menu options, and other service information. The GUI may include icons and menus, as well as other text and symbols. Keypad 711 includes an alphanumeric keypad and may represent other input controls, such as one or more button controls, dials, joysticks, touch panels, etc. The user thus can construct user profiles, enter commands, initialize applications, input remote addresses, select options from menu systems, and the like. Microphone 713 coverts spoken utterances of a user (or other auditory sounds, e.g., environmental sounds) into electronic audio signals, whereas speaker 719 converts audio signals into audible sounds.

Communications circuitry 705 may include audio processing circuitry 721, controller 723, location module 725 (such as a GPS receiver) coupled to antenna 727, memory 729, messaging module 731, transceiver 733 coupled to antenna 735, and wireless controller 737 coupled to antenna 739. Memory 729 may represent a hierarchy of memory, which may include both random access memory (RAM) and read-only memory (ROM). Computer program instructions and corresponding data for operation can be stored in non-volatile memory, such as erasable programmable read-only memory (EPROM), electrically erasable programmable read-only memory (EEPROM), and/or flash memory. Memory 729 may be implemented as one or more discrete devices, stacked devices, or integrated with controller 723. Memory 729 may store information, such as one or more user profiles, one or more user defined policies, one or more contact lists, personal information, sensitive information, work related information, etc.

Additionally, it is contemplated that mobile device 700 may also include one or more applications and, thereby, may store (via memory 729) data associated with these applications for providing users with browsing functions, business functions, calendar functions, communication functions, contact managing functions, data editing (e.g., database, word processing, spreadsheets, etc.) functions, financial functions, gaming functions, imaging functions, messaging (e.g., electronic mail, IM, MMS, SMS, etc.) functions, multimedia functions, service functions, storage functions, synchronization functions, task managing functions, querying functions, and the like. As such, control signals received by mobile device 700 from, for example, platform 103 may be utilized by API(s) 701 and/or controller 723 to facilitate remotely configuring, modifying, and/or utilizing one or more features, options, settings, etc., of these applications. It is also contemplated that these (or other) control signals may be utilized by controller 723 to facilitate remotely backing up and/or erasing data associated with these applications. In other instances, the control signals may cause mobile device 700 to become completely or partially deactivated or otherwise inoperable.

Accordingly, controller 723 controls the operation of mobile station 700, such as in response to commands received from API(s) 701 and/or data stored to memory 729. Control functions may be implemented in a single controller or via multiple controllers. Suitable controllers 723 may include, for example, both general purpose and special purpose controllers and digital signal processors. Controller 723 may interface with audio processing circuitry 721, which provides basic analog output signals to speaker 719 and receives analog audio inputs from microphone 713. In exemplary embodiments, controller 723 may be controlled by API(s) 701 in order to capture signals from camera 703 or microphone 713 in response to control signals received from platform 103. In other instances, controller 723 may be controlled by API(s) 701 to cause location module 725 to determine spatial positioning information corresponding to a location of mobile device 700. Still further, controller 723 may be controlled by API(s) 701 to image (e.g., backup) and/or erase memory 729, to configure (or reconfigure) functions of mobile device 700, to track and generate device usage logs, or to terminate services available to mobile device 700. It is noted that captured signals, device usage logs, memory images, spatial positioning information, and the like, may be transmitted to platform 103 via transceiver 733 and/or wireless controller 737. In this manner, the captured signals and/or other forms of information may be presented to users and stored to one or more networked storage locations, such as subscriber database 217 (FIG. 2), medical database 111, or any other suitable storage location or memory of (or accessible to) the components and facilities of system 100.

It is noted that real time spatial positioning information may be obtained or determined via location module 725 using, for instance, satellite positioning system technology, such as GPS technology. In this way, location module 725 can behave as (or substantially similar to) a GPS receiver. Thus, mobile device 700 employs location module 725 to communicate with constellation of satellites (not shown). These satellites transmit very low power interference and jamming resistant signals received by GPS receivers 725 via, for example, antennas 727. At any point on Earth, GPS receiver 725 can receive signals from multiple satellites, such as six to eleven. Specifically, GPS receiver 725 may determine three-dimensional geolocation (or spatial positioning information) from signals obtained from at least four satellites. Measurements from strategically positioned satellite tracking and monitoring stations are incorporated into orbital models for each satellite to compute precise orbital or clock data. Accordingly, GPS signals may be transmitted over two spread spectrum microwave carrier signals that can be shared by GPS satellites. Thus, if mobile device 700 is able to identify signals from at least four satellites, receivers 725 may decode the ephemeris and clock data, determine the pseudo range for each satellite and, thereby, compute the spatial positioning of a receiving antenna 727. With GPS technology, mobile device 700 can determine its spatial position with great accuracy and convenience. It is contemplated, however, that location module 725 may utilize one or more other location determination technologies, such as advanced forward link triangulation (AFLT), angle of arrival (AOA), assisted GPS (A-GPS), cell identification (cell ID), observed time difference of arrival (OTDOA), enhanced observed time of difference (E-OTD), enhanced forward link trilateration (EFLT), network multipath analysis, and the like.

Mobile device 700 also includes messaging module 731 that is configured to receive, transmit, and/or process messages (e.g., EMS messages, SMS messages, MMS messages, IM messages, electronic mail messages, and/or any other suitable message) received from (or transmitted to) platform 101 or any other suitable component or facility of system 100. As previously mentioned, platform 101 may transmit control singles to mobile device 700 in the form of one or more API 701 directed messages, e.g., one or more BREW directed SMS messages. As such, messaging module 731 may be configured to identify such messages, as well as activate API(s) 701, in response thereto. Furthermore, messaging module 731 may be further configured to parse control signals from these messages and, thereby, port parsed control signals to corresponding components of mobile device 700, such as API(s) 701, controller 723, location module 725, memory 729, transceiver 733, wireless controller 737, etc., for implementation.

According to exemplary embodiments, API(s) 701 (once activated) is configured to effectuate the implementation of the control signals received from platform 101. It is noted that the control signals are utilized by API(s) 701 to, for instance, remotely control, configure, monitor, track, and/or capture signals from (or related to) camera 703 and projector 702, communications circuitry 705, and/or user interface 707. In this manner, visual and/or acoustic indicia pertaining to an environment surrounding mobile device 700 may be captured by API(s) 701 controlling camera 703 and microphone 713. Other control signals to cause mobile device 700 to determine spatial positioning information, to image and/or erase memory 729, to configure (or reconfigure) functions, to track and generate device usage logs, or to terminate services, may also be carried out via API(s) 701. As such, one or more signals captured from camera 703 or microphone 713, or device usage logs, memory images, spatial positioning information, etc., may be transmitted to platform 103 via transceiver 733 and/or wireless controller 737, in response to corresponding control signals provided to transceiver 733 and/or wireless controller 737 by API(s) 701. Thus, captured signals and/or one or more other forms of information provided to platform 103 may be presented to users and stored.

It is also noted that mobile device 700 can be equipped with wireless controller 737 to communicate with a wireless headset (not shown) or other wireless network. The headset can employ any number of standard radio technologies to communicate with wireless controller 737; for example, the headset can be BLUETOOTH enabled. It is contemplated that other equivalent short range radio technology and protocols can be utilized. While mobile device 700 has been described in accordance with the depicted embodiment of FIG. 7, it is contemplated that mobile device 700 may embody many forms and include multiple and/or alternative components.

The processes described herein for healthcare management and remote examination may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 8:
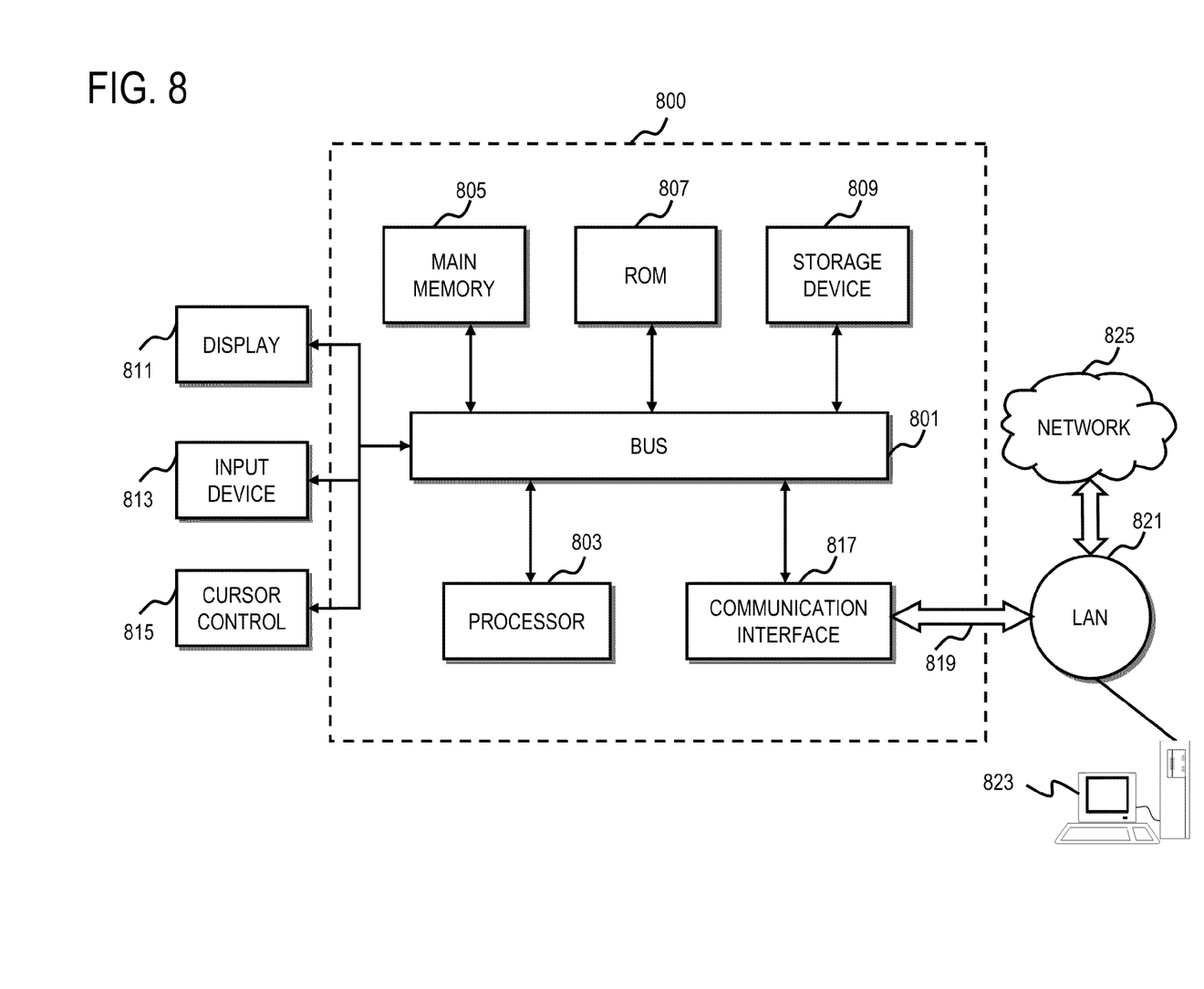
FIG. 8 is a diagram of a computer system that can be used to implement various exemplary embodiments.

FIG. 8 illustrates computing hardware (e.g., computer system) upon which an embodiment according to the invention can be implemented. The computer system 800 includes a bus 801 or other communication mechanism for communicating information and a processor 803 coupled to the bus 801 for processing information. The computer system 800 also includes main memory 805, such as random access memory (RAM) or other dynamic storage device, coupled to the bus 801 for storing information and instructions to be executed by the processor 803. Main memory 805 also can be used for storing temporary variables or other intermediate information during execution of instructions by the processor 803. The computer system 800 may further include a read only memory (ROM) 807 or other static storage device coupled to the bus 801 for storing static information and instructions for the processor 803. A storage device 809, such as a magnetic disk or optical disk, is coupled to the bus 801 for persistently storing information and instructions.

The computer system 800 may be coupled via the bus 801 to a display 811, such as a cathode ray tube (CRT), liquid crystal display, active matrix display, or plasma display, for displaying information to a computer user. An input device 813, such as a keyboard including alphanumeric and other keys, is coupled to the bus 801 for communicating information and command selections to the processor 803. Another type of user input device is a cursor control 815, such as a mouse, a trackball, or cursor direction keys, for communicating direction information and command selections to the processor 803 and for controlling cursor movement on the display 811.

According to an embodiment of the invention, the processes described herein are performed by the computer system 800, in response to the processor 803 executing an arrangement of instructions contained in main memory 805.

Such instructions can be read into main memory 805 from another computer-readable medium, such as the storage device 809. Execution of the arrangement of instructions contained in main memory 805 causes the processor 803 to perform the process steps described herein. One or more processors in a multi-processing arrangement may also be employed to execute the instructions contained in main memory 805. In alternative embodiments, hard-wired circuitry may be used in place of or in combination with software instructions to implement the embodiment of the invention. Thus, embodiments of the invention are not limited to any specific combination of hardware circuitry and software.

The computer system 800 also includes a communication interface 817 coupled to bus 801. The communication interface 817 provides a two-way data communication coupling to a network link 819 connected to a local network 821. For example, the communication interface 817 may be a digital subscriber line (DSL) card or modem, an integrated services digital network (ISDN) card, a cable modem, a telephone modem, or any other communication interface to provide a data communication connection to a corresponding type of communication line. As another example, communication interface 817 may be a local area network (LAN) card (e.g. for Ethernet™ or an Asynchronous Transfer Model (ATM) network) to provide a data communication connection to a compatible LAN. Wireless links can also be implemented. In any such implementation, communication interface 817 sends and receives electrical, electromagnetic, or optical signals that carry digital data streams representing various types of information. Further, the communication interface 817 can include peripheral interface devices, such as a Universal Serial Bus (USB) interface, a PCMCIA (Personal Computer Memory Card International Association) interface, etc. Although a single communication interface 817 is depicted in FIG. 8, multiple communication interfaces can also be employed.

The network link 819 typically provides data communication through one or more networks to other data devices. For example, the network link 819 may provide a connection through local network 821 to a host computer 823, which has connectivity to a network 825 (e.g. a wide area network (WAN) or the global packet data communication network now commonly referred to as the "Internet") or to data equipment operated by a service provider. The local network 821 and the network 825 both use electrical, electromagnetic, or optical signals to convey information and instructions. The signals through the various networks and the signals on the network link 819 and through the communication interface 817, which communicate digital data with the computer system 800, are exemplary forms of carrier waves bearing the information and instructions.

The computer system 800 can send messages and receive data, including program code, through the network(s), the network link 819, and the communication interface 817. In the Internet example, a server (not shown) might transmit requested code belonging to an application program for implementing an embodiment of the invention through the network 825, the local network 821 and the communication interface 817. The processor 803 may execute the transmitted code while being received and/or store the code in the storage device 809, or other non-volatile storage for later execution. In this manner, the computer system 800 may obtain application code in the form of a carrier wave.

The term "computer-readable medium" as used herein refers to any medium that participates in providing instructions to the processor 803 for execution. Such a medium may take many forms, including but not limited to computer-readable storage medium (e.g., non-volatile media, volatile media), and transmission media. Non-transitory media, such as non-volatile media, include, for example, optical or magnetic disks, such as the storage device 809. Volatile media include dynamic memory, such as main memory 805. Transmission media include coaxial cables, copper wire and fiber optics, including the wires that comprise the bus 801. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the embodiments of the invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

What is claimed is:

1. A method comprising:
   receiving, by one or more devices and from a user device of a medical professional, position data corresponding to a mark drawn or designated, by the medical professional and via a user interface of the user device, on an image of a subject,
      the user device and the medical professional being located remotely from the one or more devices;
   initiating, by the one or more devices and based on the position data, projection of the mark onto the subject,
      the mark specifying placement of a medical sensor by the subject or a party that is assisting the subject, and
      the medical sensor being connected to the one or more devices;
   collecting, by the one or more devices, measurement data from the medical sensor;
   receiving, by the one or more devices and from the user device, a request to stop the projection of the mark onto the subject when the medical professional eliminates, via the user interface of the user device, the mark from the image of the subject; and
stopping, by the one or more devices and based on the request, the projection of the mark onto the subject.

2. The method of claim 1, further comprising:
detecting movement of the subject;
determining a new position for the mark based on the movement; and
initiating projection of the mark at the new position onto the subject.

3. The method of claim 1, further comprising:
capturing the image of the subject; and
initiating transmission of the image to the user device.

4. The method of claim 1, further comprising:
initiating transmission of the collected measurement data for storage in a database that is accessible by the user device.

5. The method of claim 4, wherein the database is maintained by a social network service provider or a telecommunication service provider.

6. An apparatus comprising:
a memory; and
a processor configured to:
receive, from a user device of a medical professional, position data corresponding to a mark drawn or designated, by the medical professional and via a user interface of the user device, on an image of a subject,
the user device and the medical professional being located remotely from the apparatus;
initiate projection of the mark onto the subject,
the mark specifying placement of a medical sensor by the subject or a party that is assisting the subject, and
the medical sensor being connected to the apparatus;
collect measurement data from the medical sensor;
receive, from the user device, a request to stop the projection of the mark onto the subject when the medical professional eliminates, via the user interface of the user device, the mark from the image of the subject; and
stop, based on the request, the projection of the mark onto the subject.

7. The apparatus of claim 6, wherein the processor is further configured to:
detect movement of the subject,
determine a new position for the mark based on the movement, and
initiate projection of the mark at the new position onto the subject.

8. The apparatus of claim 6, wherein the processor is further configured to:
cause capturing of the image of the subject, and
initiate transmission of the image to the user device.

9. The apparatus of claim 6, wherein the processor is further configured to:
initiate transmission of the collected measurement data for storage in a database that is accessible by the user device.

10. The apparatus of claim 9, wherein the database is maintained by a telecommunication service provider for providing a telemedicine service.

11. The apparatus of claim 9,
wherein the apparatus is a mobile phone, and
wherein the apparatus further comprises:
a camera coupled to the processor and configured to generate the image; and
a projector coupled to the processor and configured to project the mark.

12. A method comprising:
receiving, by a user device of a medical professional, an image of a subject from equipment that is located remotely from the user device;
initiating, by the user device, presentation of the image via a graphical user interface;
receiving, by the user device, an input, via the graphical user interface, that draws or designates a mark on the image of the subject,
the mark specifying placement of a medical sensor by the subject or a party that is assisting the subject, and
the medical sensor being connected to the equipment;
generating, by the user device and based on the input that draws or designates the mark, a request that initiates projection of the mark onto the subject via the equipment for placement of the medical sensor;
initiating, by the user device, transmission of the request to the equipment,
the mark being projected onto the subject by the equipment based on the request;
receiving, by the user device and via the graphical user interface, another input to eliminate the mark from the image of the subject;
generating, by the user device and based on the other input to eliminate the mark from the image of the subject, another request to stop the projection of the mark onto the subject; and
initiating, by the user device, transmission of the other request to the equipment.

13. The method of claim 12, further comprising:
receiving sensor data from the equipment.

14. The method of claim 13, further comprising:
storing the sensor data in a database managed by a telecommunication service provider as a telemedicine service.

15. A system comprising:
a memory; and
one or more processors configured to:
receive an image of a subject from equipment that is located remotely from the one or more processors;
initiate presentation of the image via a graphical user interface;
receive an input, via the graphical user interface, that draws or designates a mark on the image of the subject,
the mark specifying placement of a medical sensor by the subject or a party that is assisting the subject, and
the medical sensor being connected to the equipment;
generate, based on the input that draws or designates the mark, a request that initiates projection of the mark onto the subject via the equipment for placement of the medical sensor;
initiate transmission of the request to the equipment,
the mark being projected onto the subject by the equipment based on the request;
receive, via the graphical user interface, another input to eliminate the mark from the image of the subject;
generate, based on the other input to eliminate the mark from the image of the subject, another request to stop the projection of the mark onto the subject; and
initiate transmission of the other request to the equipment.

16. The system of claim 15, wherein the one or more processors are further configured to:
   receive sensor data from the equipment.

17. The method of claim 1, wherein the one or more devices include a mobile phone.

18. The method of claim 1, wherein the medical sensor includes a medical thermometer, a blood sugar meter, a blood pressure meter, an external pacemaker, an ultrasound sensor, a stethoscope, or a combination thereof.

19. The method of claim 1, further comprising:
   receiving subsequent position data corresponding to one or more marks to be projected onto the subject;
   initiating projection of the one or more marks onto the subject; and
   collecting additional measurement data from the medical sensor after initiating the projection of the one or more marks onto the subject.

20. The apparatus of claim 11, wherein the projector is built in the apparatus.

21. The method of claim 12, further comprising:
   performing an authentication procedure for the subject based on at least one of:
      a user identification (ID)
      a password, or
      a biometric identification.

22. The system of claim 15, wherein the one or more processors are further configured to:
   establish a videoconferencing session between a medical professional and the subject.

\* \* \* \* \*